United States Patent [19]

Moulder

[11] Patent Number: 5,267,940
[45] Date of Patent: Dec. 7, 1993

[54] CARDIOVASCULAR FLOW ENHANCER AND METHOD OF OPERATION

[75] Inventor: Peter V. Moulder, New Orleans, La.

[73] Assignee: The Administrators of the Tulane Educational Fund, New Orleans, La.

[21] Appl. No.: 695,946

[22] Filed: May 6, 1991

Related U.S. Application Data

[63] Continuation-in-part of Ser. No. 442,712, Nov. 29, 1989, abandoned.

[51] Int. Cl.$^5$ .................... A61F 2/00; A61N 1/362
[52] U.S. Cl. ................................ 600/16; 600/17; 623/3; 604/8; 604/9
[58] Field of Search .......................... 623/1–3; 604/8, 9; 600/16, 17, 18, 36; 137/569

[56] References Cited

U.S. PATENT DOCUMENTS

| | | | |
|---|---|---|---|
| 2,049,233 | 7/1936 | Thomas | 137/569 X |
| 2,203,980 | 6/1940 | Burt | 137/569 X |
| 2,456,566 | 12/1948 | Plank | 137/569 X |
| 3,435,824 | 4/1969 | Gamponia | 604/8 |
| 3,487,784 | 1/1970 | Rafferty et al. | 623/3 X |
| 3,505,987 | 4/1970 | Heilman | 623/3 X |
| 3,608,088 | 9/1971 | Dorman et al. | |
| 3,746,027 | 7/1973 | Elliott | 137/569 X |
| 3,911,897 | 10/1975 | Leachman, Jr. | 600/17 |
| 3,911,898 | 10/1975 | Leachman, Jr. | 600/17 |
| 4,014,318 | 3/1977 | Dockum et al. | |
| 4,105,016 | 8/1978 | Donovan, Jr. | 600/16 |
| 4,135,253 | 1/1979 | Reich et al. | 600/16 X |
| 4,195,623 | 4/1980 | Zeff et al. | 604/9 X |
| 4,245,622 | 1/1981 | Hutchins | |
| 4,389,737 | 6/1983 | Robinson et al. | |
| 4,527,549 | 7/1985 | Gabbay | |
| 4,813,952 | 3/1989 | Khalafalla | 623/3 |
| 4,892,539 | 1/1990 | Koch | 623/1 |
| 4,938,766 | 7/1990 | Jarvik | 623/3 |
| 4,968,293 | 11/1990 | Nelson | 604/8 X |

FOREIGN PATENT DOCUMENTS

| | | | |
|---|---|---|---|
| 22585 | 1/1962 | German Democratic Rep. | 137/569 |

Primary Examiner—Randall L. Green
Assistant Examiner—Mary Beth Jones
Attorney, Agent, or Firm—Wood, Phillips, VanSanten, Hoffman & Ertel

[57] ABSTRACT

An implanted cardiovascular assist pump is connected with the proximal descending thoracic aorta. The pump inlet is connected with the aorta at substantially the site of the first pressure/flow node from the heart. The pump outlet is connected at substantially the site of the last pressure/flow antinode before the heart. Control of pump speed varies blood flow through the pump. As a fail-safe mechanism, a pump shunt flow path is provided, through one of a variety of disclosed structures.

23 Claims, 6 Drawing Sheets

FIG. IA
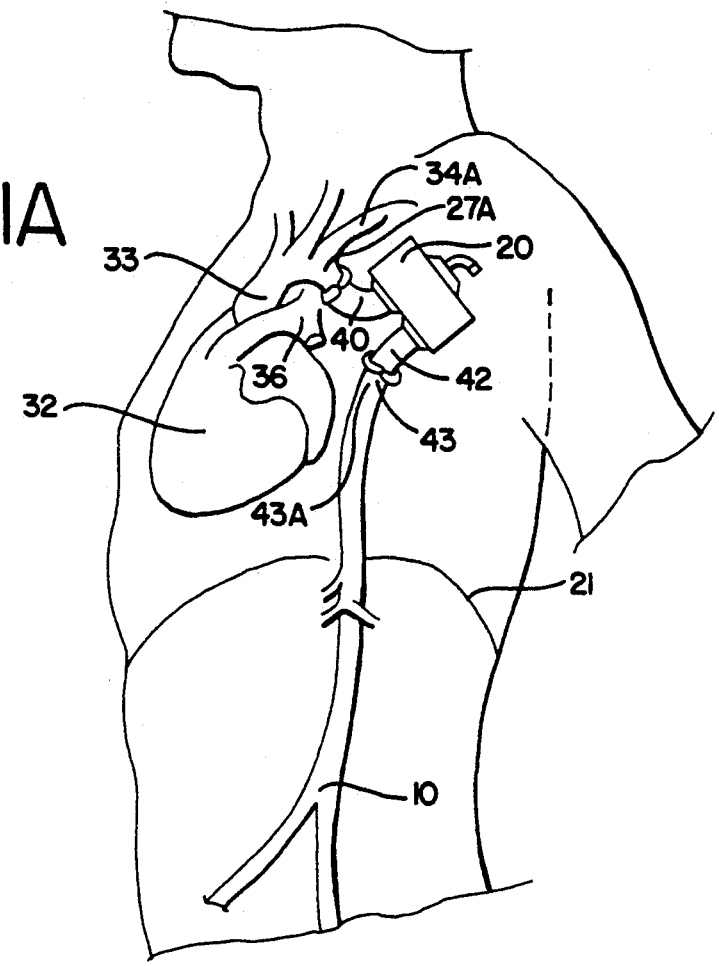
FIG. IB
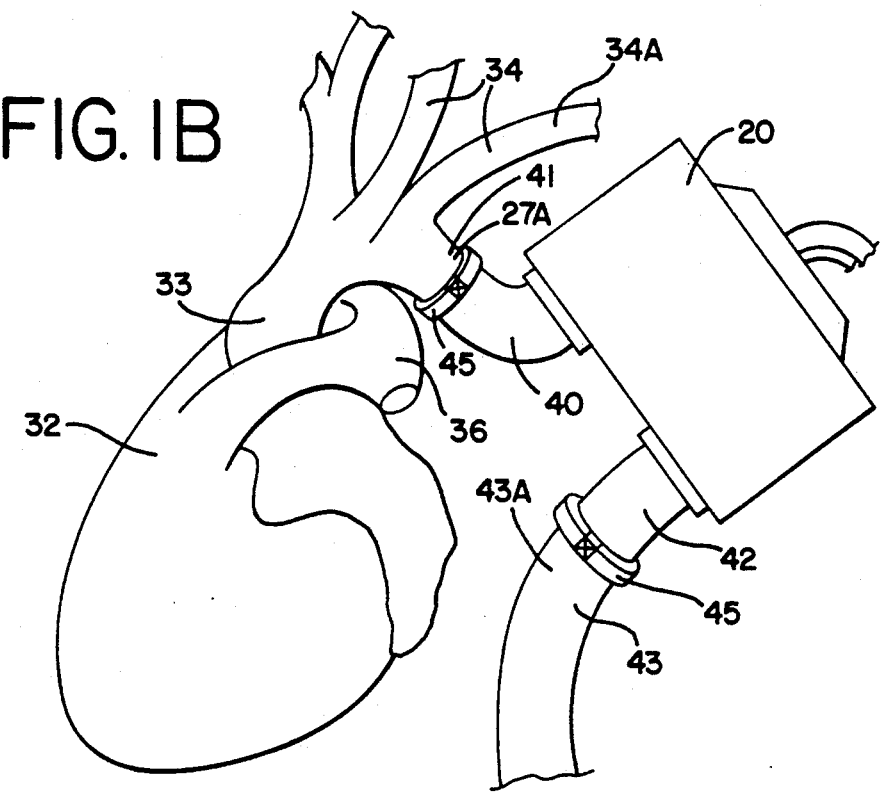

RESTRICTED SHUNT FLOW

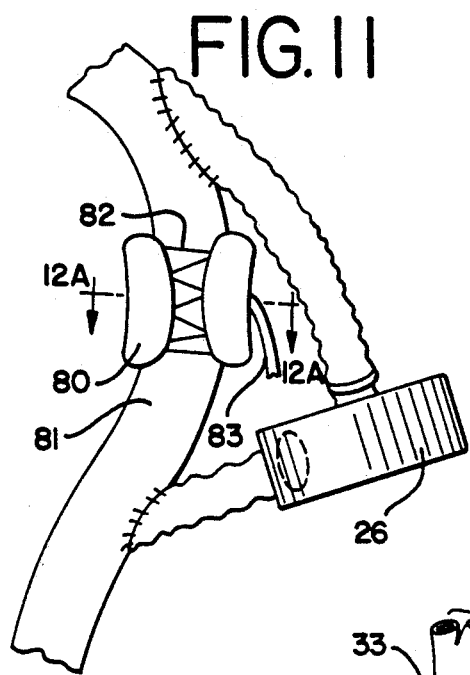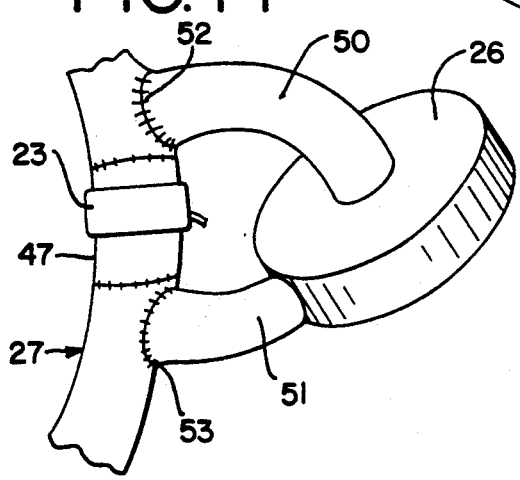

5,267,940

CARDIOVASCULAR FLOW ENHANCER AND METHOD OF OPERATION

This is a continuation in part of application Ser. No. 442,712 filed Nov. 29, 1989, now abandoned.

FIELD OF THE INVENTION

This invention relates to a cardiovascular flow enhancer particularly intended for permanent implantation in a subject whose heart requires assistance.

BACKGROUND OF THE INVENTION

Many heart patients have partial heart function and could benefit from a chronic or long-term ventricular assist device. There is no such chronic assist device in use at this time. Artificial hearts, either complete or partial, have been implanted as a temporary bridge to a heart transplant. These devices replace rather than assist normal heart function. Two main categories of assist devices are being developed and analyzed. One utilizes portions of an artificial heart or a comparable apparatus connected between the heart and aorta. These devices, although they are implanted and use an internal power source, are intended as a short term bridge to a transplant. The other category is counter pulsation devices which attach to the aorta. Blood flows passively to a collapsible chamber during systole. The chamber is then collapsed and the blood forcibly returned to the aorta.

Acute or short term ventricular assist devices presently used are of two principal types. Neither is used for chronic use. One has a counter pulsation action and is exemplified by use of an intra-aortic balloon. The balloon is collapsed during systole, providing an empty space to be filled with blood pumped by the heart. As the space is empty, the heart operates against little resistance. The balloon is then expanded, forcing blood through the arterial system. This type of ventricular assist is unsuitable for chronic use as it requires a pneumatic connection through the subject's skin for contraction and expansion of the balloon. Infection is likely to occur. The second type of acute assist device utilizes an extracorporeal pump, as the Biomedicus centrifugal pump. Again, connection through the skin is required for the pump inlet and outlet with a risk of infection. In both such systems, vigorous anticoagulation therapy, which is not feasible for long term use, is required.

BRIEF SUMMARY OF THE INVENTION

A principal feature of the invention is an implantable cardiac assist device for chronic or long term use. It employs no valves that may promulgate clotting and will require only minimal ongoing anticoagulation therapy.

More particularly, a prime feature of the invention is a flow enhancer which includes an implanted centrifugal pump having an inlet connected at the site of the nodal point of the descending thoracic aorta. The nodal point is a unique site offering unique advantages: with a supplemental pump connected at the site of the first pressure/flow node, the forward flow of blood from the left ventricle of the heart is complemented through acceleration at this point; immediately proximal to the nodal site, reflected waves from two major sites, the abdominal aorto-iliac junction and the collection of small peripheral arteries, coalesce to produce a major disturbance to flow; with a supplemental pump connected at this site, reflected flow and pressure from these sites will be eliminated and the deleterious effects of the reflected flow and pressure removed; and improvement of blood flow in this section of the descending thoracic aorta is particularly beneficial as nearly seventy percent of blood flow passes through this section of the aorta.

Further advantages result from connecting the centrifugal pump inlet to the nodal point in the descending thoracic aorta. So connected, the harmful effects of any aortic stiffness or lack of compliance may be overcome. A large part of myocardial energy is expensed in filling the distending aorta. Compliance is a major determinant of aortic impedance or resistance. Connecting the centrifugal pump at the nodal point makes possible the compliance release effects of the present invention. As the ventricular output arrives at the aorta, the release offered by the centrifugal pump system mimics easy distensibility of the aorta, thus further reducing the workload of the heart. Thus, the present invention enhances the pressure/flow dynamics of the cardiovascular system instead of overriding or interfering with those dynamics, as in the case of the prior art.

Another advantage resulting from connecting the centrifugal pump inlet to the nodal site in the descending thoracic aorta is that cardiac effort is drastically reduced, thus allowing the heart to work with improved loading and contractile characteristics so that it can heal and improve. In contrast, use of prior art systems does not promote healing of the heart muscle but instead risks further loss of myocardial function. Ventricular bypass systems supersede cardiac effort to the extent that the heart muscle will atrophy, and although counterpulsation devices are helpful during systole, the counterpulsed flow is completely contrary and hard on the heart during dastole.

A further advantage results from connecting the centrifugal pump inlet to the nodal point in the descending thoracic aorta. No cardiac or pericardial intrusion is required, preserving a virgin -ericardial sac. This feature is advantageous in that it presents a great safety factor for subsequent surgery, such as coronary artery bypass surgery when the heart has improved or cardiac transplantation, should it become available, and, if adequate improvement is not achieved.

A further advantage results from connecting the centrifugal pump inlet to the nodal point in the descending thoracic aorta. All connections to the aorta are specifically made downstream of the arteries serving the brain, lungs and heart. In the unlikely event that clots would form or debris would be generated in the pump or associated components, and those clots or debris would be discharged into the bloodstream, such discharge would occur downstream of those critical arteries, and no cerebral, pulmonary or cardiac embolism would occur.

Another feature is that the pump is implanted either in the lower posterior chest, more particularly in the lower left hemithorax above the diaphragm, or in the upper posterior thorax behind the upper lobe. Each site occupies an insignificant portion of the left hemithorax. Note, however, that although the implantation site may vary, the connection site will remain the same.

Another unique feature of the invention results from the use of an efficient centrifugal pump with no valves. First, use of a centrifugal pump having no valves lessens the opportunity for damaging the blood. Secondly, such a pump may be used in combination with a device for controlling the speed of the pump, to complement the pumping action of the heart, and to change pump speed in response to selected physiological conditions.

A further feature of the flow enhancer for rare usage is a shunt potential to allow normal blood flow during any mechanical failure of the pump or blockage of the fluid flow path through the pump. In order to accomodate patients in any stage of arterial deterioration, a number of such shunts are described, some even utilizing the aorta, to afford backup potential for normal blood flow. For example, a section of the thoracic aorta or of a graft conduit in series with the aorta may be connected to provide a shunt flow path parallel to the path through the pump. In normal operation of the pump, blood flow through the shunt flow path would be minimal, sufficient simply to prevent clotting. However, in case of pump failure or blockage as described, the shunt opens to allow blood flow through the shunt. The provision of an emergency shunt path is thus advantageous in that with failure of the pump flow path and the resultant opening of the shunt, the patient would simply return to his preoperative condition and could sit or lie down if need be and would not be further impaired by the existence of a failed implanted device.

One alternative emergency shunt system employs a controllable occluder which opens when flow through the pump falls below a minimum level. The occluder may be provided on a graft in series with the aorta, on the aorta itself, or may be on a conduit between the inlet and outlet conduits of the pump. A second alternative is a nearly closed long tube which would function as a small shunt with minimal flow during normal operation but which would snap into a short tube with a wide diameter at pump failure or blockage to allow complete shunted flow. A third alternative employs a weighted check valve in the aorta which would remain closed during normal operation, but which would open in case of pump failure by normal aortic flow pressure; this check valve also prevents back flow of blood discharged from the centrifugal pump.

Further features and advantages of the invention will readily be apparent from the following specification and from the drawings, in which:

FIG. 1A is an oblique view of the subject illustrating an encapsulated pump, shunt, drive motor and blood flow channels in the upper posterior hemithorax;

FIG. 1B is an enlarged view of the heart and the descending thoracic aorta with the encapsulated pump of FIG. 1A connected to the nodal point of the descending thoracic aorta;

FIGS. 11 and 12 are similar to FIGS. 7 and 8 showing yet another form of occluder;

FIG. 13 is an enlarged view of the heart and a section of the descending thoracic aorta with the pump connected in parallel with the descending thoracic aorta, which is occluded during normal operation, to provide an emergency blood flow route in the event of failure of the primary blood flow route through the pump;

FIG. 14 is a fragmentary drawing illustrating an example of an emergency failure shunt system showing the pump connected in parallel with an occluder graft in the aorta, which severely restricts blood flow during normal operation, to provide an emergency blood flow route in the event of failure of the primary blood flow route through the pump;

FIG. 15 is a fragmentary view of the aorta showing an outlet conduit from the pump with a T-graft to the aorta for use in an emergency failure shunt system;

Many subjects have heart muscle damage that results in a limited pumping capability. This restricts the subject's physical activity, promotes damage to other organs, reduces the subject's overall feeling of well-being, and in the most severe cases the subjects are bedridden and require consideration of a heart transplant. In subjects having heart muscle damage it is desirable to reduce the detrimental factors which contribute to the decreased efficiency of the damaged heart while providing sufficient blood flow to the remainder of the body.

Some of these detrimental factors relate to the dynamics of the pressure waves produced by the beating heart. The beating heart produces a train of flow and pressure waves traveling downstream throughout the aorta and the vascular bed. With the aorta dividing into smaller diameter branches at the iliac junction 10 (shown in FIG. 1A), and further downstream, the pressure and flow waves are reflected back toward the heart from this junction, as well as from the arterial bed itself. These reflected pressure and flow waves interfere with the incident pressure and flow waves produced by the beating heart, decreasing the heart's efficiency.

Others of these detrimental factors relate to the stiffness of the descending aorta. The stiffness, or lack of compliance, in the descending aorta contributes to an increased resistance, or impedance, of the aorta to blood flow.

In the present invention, the effects of the aforementioned detrimental factors are eliminated through the use of a unique site on the aorta for connection to the flow enhancer. The flow enhancer reduces the load on the heart and provides increased blood flow, allowing greater subject activity. The flow enhancer may be implanted for a long term supplementation of the damaged heart. The subject is spared the risk and expense of a heart transplant.

Briefly, a pump, preferably a variable speed centrifugal pump, power supply and control are implanted. The pump is connected with the subject's vascular system in a novel manner as will be described in more detail below.

Figure 1C:
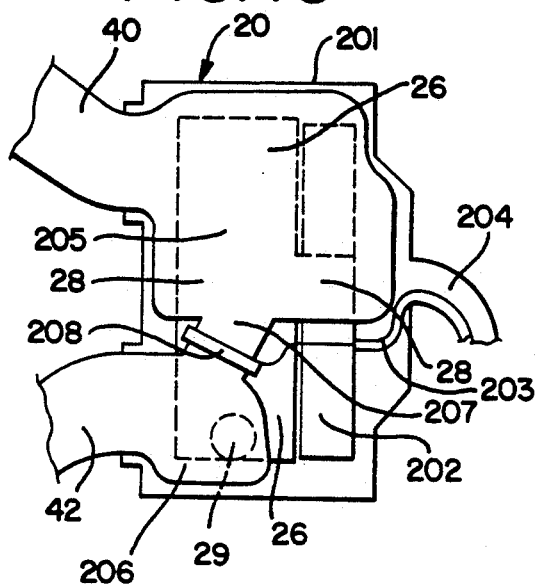
FIG. 1C is a cross section of a pump encapsulated with a drive motor, blood flow channels, shunt and occluder.
Figure 1D:
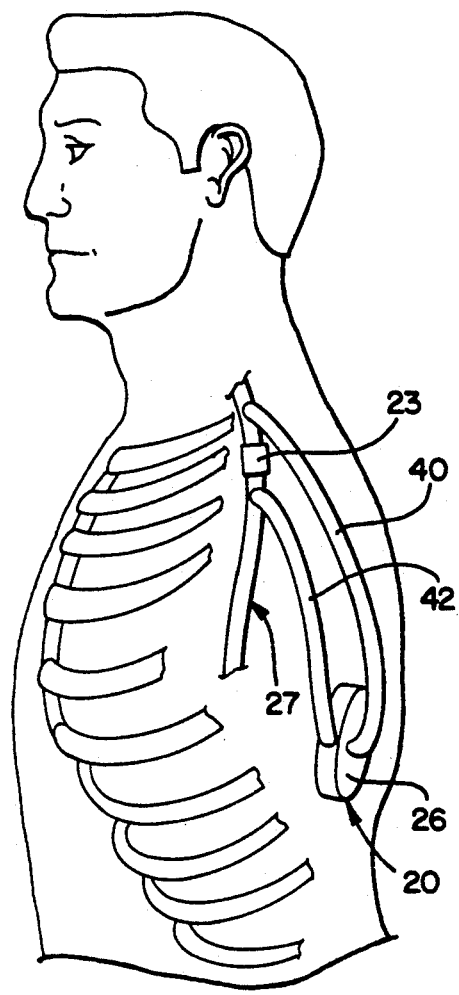
FIG. 1D is a side view of a subject illustrating an alternative embodiment of the invention, with the pump located in the lower posterior hemithorax but with the connection to the aorta in the same places as FIGS. 1A and 1B; the pump shown in FIGS. 1C and 2 is not encapsulated with the emergency shunt, and the shunt is instead shown separately.
Figure 2:
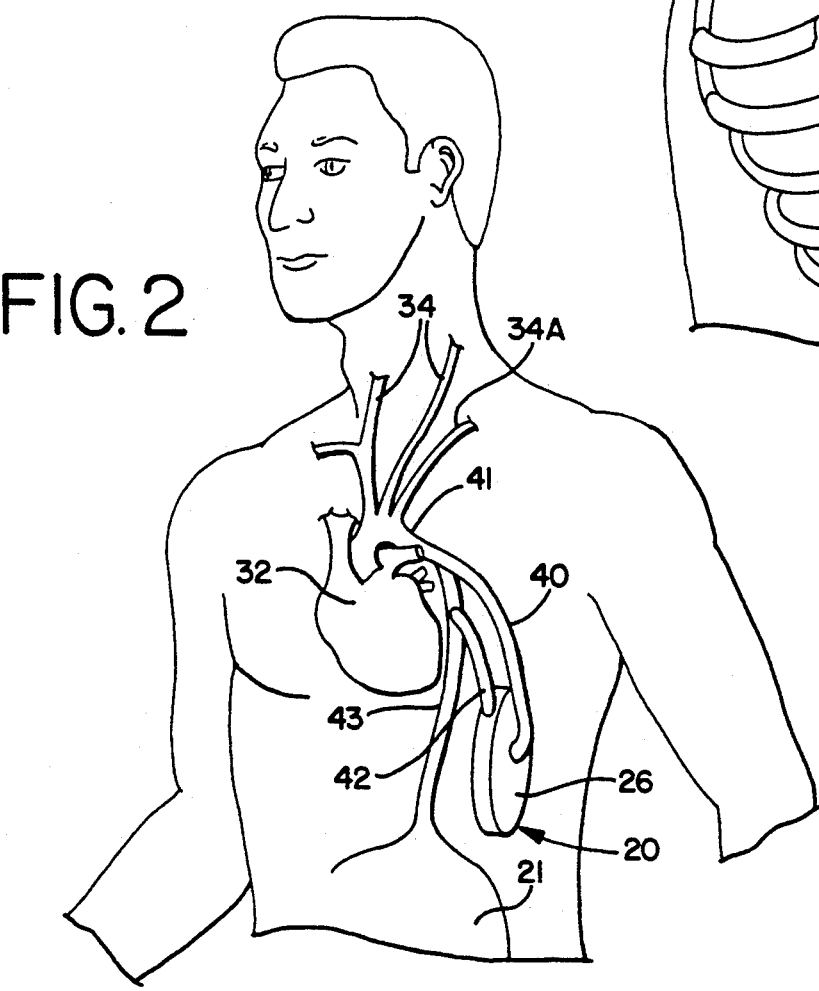
FIG. 2 is an oblique view of FIG. 1D.

Although the connections to the aorta are always in the same location for each embodiment of the invention, alternative locations of the implant 20 are illustrated in FIGS. 1A, 1D and 2. In FIG. 1A and 1B, the implant 20 is in the upper posterior thorax behind the upper lobe. In FIGS. 1D and 2, the implant is behind and below the heart 32 and left lung (not shown); more specifically, in FIGS. 1D and 2, it is in the lower, lateral intrathoracic supradiaphragmatic location, above the diaphragm 21. Each of these sites occupies an insignificant portion of the left hemithorax. In all cases, the implant 20 is connected with the descending thoracic aorta 27 as will be described.

Various forms of implants may be utilized in the invention. An illustrative encapsulated implant 20 is shown in FIG. 1C as including within an outer case 201, made of a biologically inert material, a pump 26 driven by a drive motor 202 which receives power and control through wires 203. A pressure equalization tube 204 exits the outer case 201 and terminates, for example, in a subcutaneous gas exchange unit (not shown). The pump 26 has one or more axial inlets 28 and tangential outlets 29. Inlet and outlet conduits 40, 42, are in fluid connection with the pump inlets 28 and outlets 29. At the pump inlets 28, the inlet conduit 40 defines an inlet chamber 205 which substantially surrounds a portion of the pump, and the outlet conduit 42 defines an expanded outlet chamber 206 to receive blood from the pump outlet 29. An emergency shunt path 207 is provided to bypass the pump in emergencies. The shunt path 207 is normally held nearly closed, with only enough flow to prevent clotting, by occluder 208, and provides a blood flow path between the inlet chamber 205 and the outlet chamber 206.

It should be understood that a variety of configurations are available for an encapsulated implant, and that a particular encapsulated implant may contain more or less than the components shown in FIG. 1C, may provide various blood flow channels, and need not provide an internal shunt path. Furthermore, the pump need not be encapsulated with other components. As illustrated in FIGS. 1D and 2-17, the pump 26, with its outlet 28 and outlet 29, although preferably covered with or comprising a biologically inert material, is not encapsulated with other components.

For all of the illustrated embodiments, pump 26 is a centrifugal pump preferably of the two-stage construction disclosed in Findlay, Ser. No. 402,676 filed Sep. 5, 1989, now abandoned, and its continuation-in-part, Ser. No. 659,859, filed Feb. 22, 1991 now U.S. Pat. No. 5,174,726, both assigned to the assignee of this invention. This pump is designed to have no valves which could damage the blood.

Figure 3:
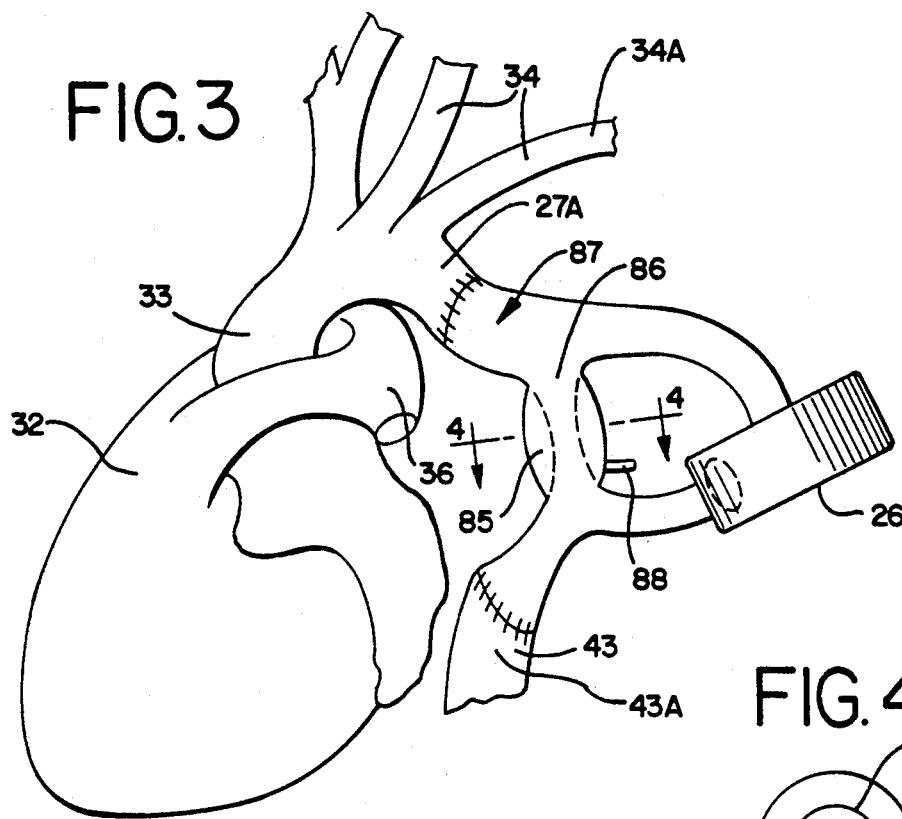
FIG. 3 is a view of the heart and the descending thoracic aorta showing the pump connected in parallel with a flow controlling occluder on a graft to the aorta to provide an emergency blood flow route in the event of failure of the primary blood flow route through the pump.

Extending upwardly from heart 32, FIGS. 1 and 3, is the ascending aorta 33. The brachiocephalic arteries 34, FIGS. 1B and 3, extend upwardly from the ascending aorta, and above the pulmonary artery 36. Of the brachiocephalic arteries 34, the left subclavian artery 34A is most proximate to the connection between the pump inlet 28 and the descending thoracic aorta.

The inlet conduit 40 connects pump inlet 28 with the inlet portion 41 of the descending thoracic aorta. The pump outlet 29 is connected through conduit 42 with the outlet portion 43 of the descending thoracic aorta. The connections between the conduits and pump may be completed with ring clamps 45. The connections between the aorta and conduits may be completed with ring clamps 45 or by sutures.

In the present invention, cardiovascular flow advantages and other advantages are achieved in part through the unique connection site of the centrifugal pump in the aorta. The unique connection site offers substantial benefits, not only in mechanically assisting the heart in its pumping function, but also in decreasing the resistance, or impedance, to the heart's pumping of the blood and in preserving a virginal pericardial sac. Preservation of a virginal pericardial sac is beneficial in that it presents a great safety factor for subsequent surgery, such as coronary artery bypass surgery when the heart has healed and improved or cardiac transplantation surgery, should it become necessary if adequate improvement is not achieved.

As shown in FIGS. 1A-3, the input and output of the centrifugal pump 26 are located outside of the pericardium, in the descending thoracic aorta 27, downstream from and proximal to the brachiocephalic arteries 34. The preferred connection of pump inlet conduit 40 with the thoracic aorta 27 is at the nodal point, a site of minimal pressure or flow fluctuation in the upper portion of the descending thoracic aorta. The outlet conduit 42 is connected with the outlet section 43 of the descending thoracic aorta at substantially the site of the antinodal point 43A. With these connection sites, pump 26 is particularly efficient in supplementing flow of blood from the heart by acceleration of flow at the most efficient flow form and by negating the deleterious effect of pressure and flow reflections.

The pressure/flow nodal and antinodal points of a subject vary primarily with heart rate and on occasion the antinode may be upstream of the node. The connection points for the inlet and outlet conduits are therfore not critically defined, and can be made within a length of the aorta of some three to five inches.

Generally, the nodal point of the descending thoracic aorta is four to five centimeters long and lies within an eight to ten centimeter range commencing about one to two centimeters downstream of the left subclavian artery 34A, the last of the brachiocephalic arteries 34.

The nodal point of a subject represents an important hemodynamic site. This point of the aorta has been variously described as the lowest point in the sinusoidal summed reflections or even as a site of no reflection, and as the site at which the ventricular unit ejection volume fills and distends the aorta to give it potential energy for the next forward movement of blood in the cardiac cycle (the "Windkessel" theory).

Shortly below—or perhaps concurrent with—the first node site is the last antinode site, where the major summed flow and pressure wave reflections from the aortic bifurcations and peripheral vascular beds arrive. This antinode is the site of the return blood to the aorta from the centrifugal pump's discharge. Thus, the effect upon the heart of the entire mass of flow and pressure wave reflections from the aortic bifurcations and the peripheral vascular bed is eliminated by the present invention.

I have discovered that utilizing this nodal site on the descending thoracic aorta offers unique advantages, in particular for an active device such as the centrifugal pump of the present invention. By withdrawing blood for pumping at this site on the aorta, and simultaneously preventing backflow of blood at this site, a pump connected at this location offers the advantage of preventing reflected pressure and flow waves from the iliac junction, vascular beds, and other locations from retarding the forward flow of blood, and preventing these reflected waves from truncating the incident waves produced by the beating heart. In addition, by providing supplemental pumping from this site, the resistance, or impedance, to flow seen by the heart for the region downstream of this site is eliminated. Because some seventy percent of blood flow and a greater percentage of the heart's workload is directed to this region, this dramatically reduces the workload of the heart. Furthermore, supplemental pumping at this site provides a voluminous capacitance in the aorta for receipt of each ventricular ejection, thus further reducing the heart's workload.

In my experience as a cardiovascular surgeon, I have implanted valves such as the Hufnagel valve at this site in treating patients suffering from impairment of heart valve function. The Hufnagel valve is a passive device, comprising a caged ball and a valve seat; such a valve is essentially a check valve prohibiting back flow toward the heart. I have placed such valves in the descending thoracic aorta, outside the pericardium, beyond the brachiocephalic arteries, in the nodal/antinodal site described above. Surprisingly effective results were obtained when this valve was installed at this site because the valve not only assumed the role of the damaged heart valve but eliminated the adverse effects of the antinode back pressure and flow as well.

The major portion of the descending thoracic aorta 27, down near the diaphragm, visibly jumps and pulses along its length. To the knowledgeable eye, a substantially non-pulsing or quiescent site can be observed just downstream of the left subclavian artery. This quiescent area is the site of the first node and last antinode of the descending thoracic aorta.

Experiments I have conducted in dogs have demonstrated that the advantages of this connection site for the centrifugal pump are obtained without disrupting the blood pressure dynamics necessary to maintain flow through the brachiocephalic arteries 34 and coronary arteries (not shown).

As shown in FIG. 1A, the centrifugal pump 26 is connected in series with the heart 32, with the pump inlet 28 connected to receive blood from the descending thoracic aorta at the site of the nodal point 27A, and with the pump outlet 29 connected to discharge blood to the descending thoracic aorta 27 at a point downstream from the inlet connection 27A. Ring clamp connectors 45, of the type used with devices such as the Hufnagel valve, may be used to connect the aorta to the pump.

Although implantation of the centrifugal pump as described above and shown in FIGS. 1A and 1B will effectively achieve the above-described cardiovascular flow advantages, it may be desirable to provide a failsafe mechanism in the event of pump failure or blockage. For example, if the centrifugal pump should fail because of some mechanical problem, or if clotting, debris or some other factor should reduce or stop flow through the pump or its inlet or outlet, it would be desirable to provide a means of bypassing the pump so that the blood supply in the aorta could be maintained in such emergency situations. Although some flow will occur through an unobstructed but non-rotating centrifugal pump, an emergency bypass will permit the system to fail in a safe condition.

To provide an emergency bypass system to assure continued blood flow, various configurations of emergency shunt failure systems may be used in combination with a centrifugal pump connected to the nodal point of the descending thoracic aorta. The connection of pump 26 with a shunt flow path affords an opportunity for control of the relative flow of blood in two paths. In general, one path is provided for flow of blood from the first node on the descending aorta, through the pump and back to the aorta downstream of the pump inlet; the second path is generally provided as an emergency flow path parallel to the first path. For example, a section of the thoracic aorta 27 (or of a graft conduit in series with the aorta) may be connected in shunt with the pump. In case of either mechanical or power failure as described, the emergency shunt opens to allow blood flow through the shunt. Several alternative emergency shunt systems are illustrated in the accompanying drawings.

Various forms of pump connections, shunts and occluders are illustrated to aid in handling aortas in various stages of disease, calcification and friability.

Figure 4:
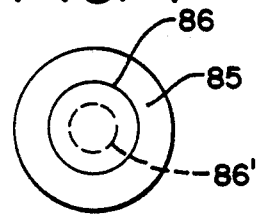
FIG. 4 is a section along line 4—4 of FIG. 3 showing operation of the occluder.

One alternative emergency shunt system, illustrated in FIGS. 3 and 4, utilizes a controllable occluder to open a secondary flow path in the event of blockage or failure of the primary flow path. An occluder 85 is incorporated in the wall of a shunt flow passage 86 of a series graft 87, as in FIG. 3. Pressure in line 88 actuates the occluder to collapse the flow passage 86 to the position 86', as seen in FIG. 4 for normal operation of the system with maximum flow through the pump and minimal flow through the passage 86. A release of pressure in line 88 will deactivate the occluder to allow the flow passage 86 to open for flow through the shunt path in emergencies.

Figure 5:
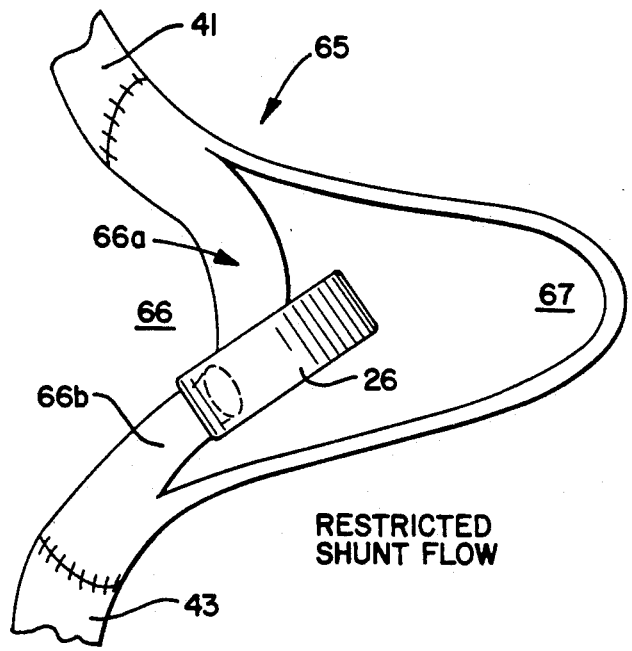
FIG. 5 is a fragmentary view illustrating an example of an emergency shunt failure system showing the pump and an accordion graft externally held in the extended (closed) position and acting as an emergency shunt, connected in parallel with the pump to provide an emergency blood flow route in the event of failure of the primary blood flow route through the pump.
Figure 6:
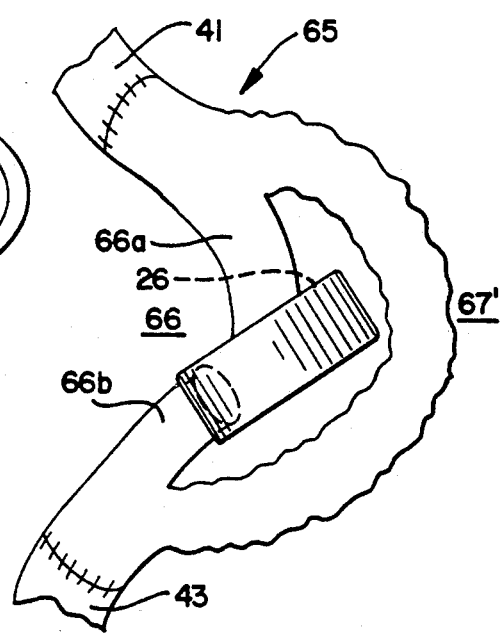
FIG. 6 is a fragmentary view similar to FIG. 5 showing the accordion shunt graft after the pump has failed and blood pressure from the beating heart has opened the shunt.

A second alternative emergency shunt system, illustrated in FIGS. 5 and 6 is a nearly closed long tube which would be externally held in that configuration and would function as a small shunt during normal operation, allowing only minimal blood flow to preclude clotting, but which would be snapped into a short tube with wide diameter by pressure from the beating heart at pump failure or blockage to allow complete shunted flow. As shown in FIG. 5, a graft 65 is connected in series between the upper section 41 and lower section 43 of the thoracic aorta. The graft has a first flow passage 66 with an upper section 66a connected with the inlet of pump 26 and the lower section 66b connected with the outlet of the pump. A second accordion flow passage 67 is in shunt with pump 26. The relative flow characteristics through the pump and shunt may be controlled by selecting the length and diameter of the two flow passages. In FIG. 5, the second flow passage 67 is longer and has a smaller inner diameter than the flow passage 67' of FIG. 6. Accordingly, FIG. 5 illustrates the normal state of the implant, with flow through the path 66 containing the pump 26; there is minimum blood flow through the second passage 67 and maximum flow through the first passage and pump 26. In the event that flow through the first flow passage 66 falls below a minimal level, the second flow passage 67 distends and shortens due to pressure; the implant reaches the state illustrated in FIG. 6, with the second flow passage 67' having a greater diameter to allow blood to bypass the first flow path 66.

The shunt configuration shown in FIG. 3, as well as in FIGS. 5 and 6, are advantageous in that the tubular members of the composite unit may be manufactured prior to implantation, with the connections made to the aorta at implantation. Such an arrangement should allow for rapid connection by an experienced surgeon.

Figure 7:
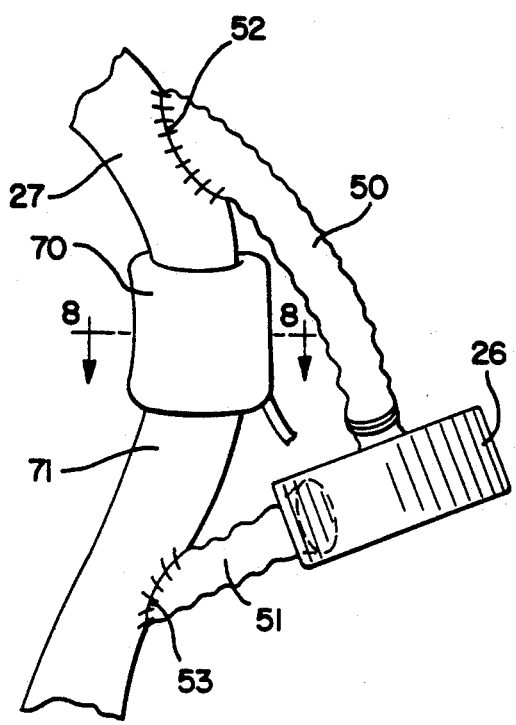
FIG. 7 is a fragmentary view showing the pump connected in parallel with a flow controlling occluder on the aorta to provide an emergency blood flow route in the event of failure of the primary blood flow route through the pump.
Figure 8A:
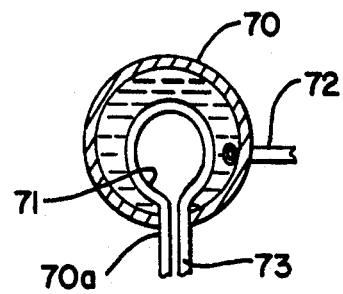
FIGS. 8A and 8B are sections taken along line 8—8 of FIG. 7 illustrating operation of the occluder.
Figure 8B:
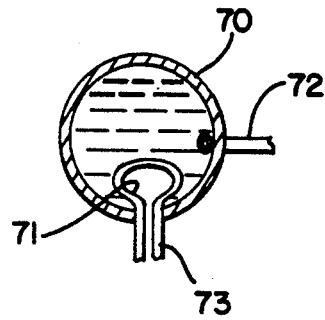

In FIG. 7, another emergency shunt connection is illustrated. Here, inlet conduit 50 and outlet conduit 51 are connected to the thoracic aorta 27 with side-to-end sutured grafts 52, 53 respectively. A controllable flow occluder 70 is mounted on the section of aorta between the two grafts. The occluder 70, as seen in FIGS. 8A, 8B is a collar connected with a source of pressurized fluid (not shown) through a control line 72. The diameter of the flow passage through aorta 71 may be controlled by varying the fluid pressure inside the collar 70. In FIG. 8A the aorta is open allowing maximum blood flow, as in emergency situations. In FIG. 8B, the pressure of the fluid within collar 70 is increased, reducing the diameter of aorta 71 to allow only enough blood flow to prevent clotting, as in the normal operation of the system. Occluder collar 70 is provided with an opening 70a to accommodate branch artery 73.

Figure 9:
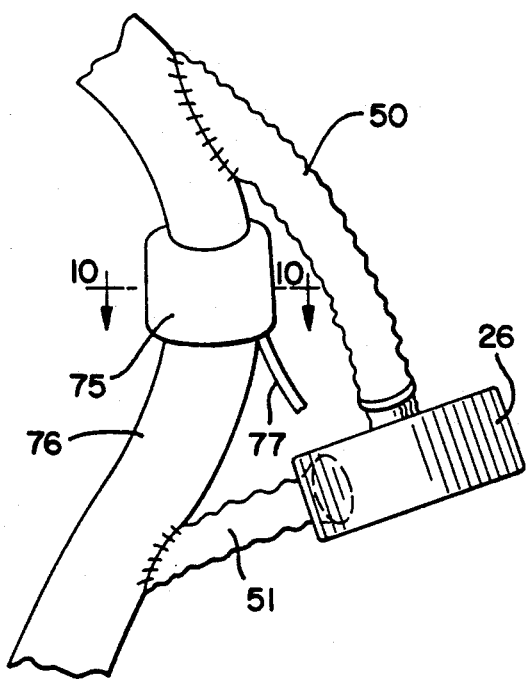
FIGS. 9 and 10 are similar to FIGS. 7 and 8, showing another form of occluder.
Figure 10A:
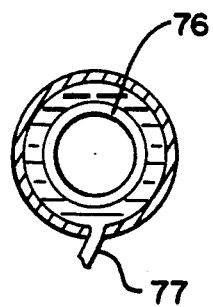
Figure 10B:
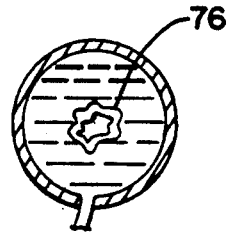

In FIG. 9 the occluder 75 is located on a section 76 of the aorta where there is no branch artery. Collar 75 completely surrounds aorta 76 and, by application of pressure through line 77 the aorta is almost completely collapsed as illustrated in FIG. 10B.

In FIG. 11 a two-section occluder 80 effects anterior-posterior compression of aorta section 81. Occluder 80 has two pads 80a, 80b which are secured on the aorta by elastic filaments 82, FIGS. 11, 12A. When the pads are subjected to pressure through line 83 the pads collapse as shown in FIG. 12B. This flattens the aorta 81 and is particularly effective for a subject with a partially calcified aorta as indicated at 84.

In another alternative emergency shunt system, illustrated in FIG. 13, a variable occluder 23 is mounted on the section 24 of the descending thoracic aorta between the connections for the inlet conduit 40 and outlet conduit 43. Control of the occluder, described above, establishes the relative flow between the pump 26 and aorta section 24 to allow for blocking flow through the section 24 of the aorta during normal operation and to allow for emergency flow through the section 24 of the aorta when the occluder is opened. To prevent clotting, the occluder allows for a small amount of blood flow through the aorta at all times.

Another shunt connection of pump 26 to a graft 47 in thoracic aorta 27 is illustrated in FIG. 14. Here, inlet conduit 50 and outlet conduit 51 are connected with the wall of the aorta using side-to-end sutured grafts 52, 53 respectively. Occluder 23 controls flow through the graft 47.

Figure 16:
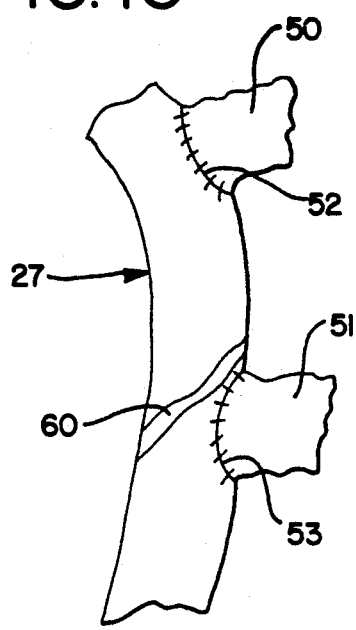
FIG. 16 is a fragmentary view showing the pump connection similar to FIG. 13, with a check valve in the aorta.
Figure 17:
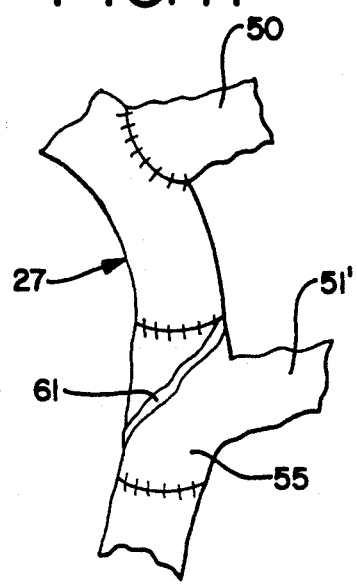
FIG. 17 is a fragmentary view similar to FIG. 15 showing a check valve in a T insertion.

Another alternative emergency shunt system, shown in FIGS. 16 and 17, employs a weighted flap check valve 60 in the thoracic aorta 27 which would remain nearly closed during normal operation, but which would open by normal aortic flow pressure in the event that flow through the pump falls below a minimum level. The valve 60 also prevents retrograde flow of blood through the aorta. As shown in FIG. 16, the inlet conduit 50 and the outlet conduit 51 are connected with the wall of the aorta using side-to-end sutured grafts 52, 53, and a flap check valve 60 is placed in the thoracic aorta 27 between the connection.

Instead of side-to-end grafts, the outlet conduit 51' of the pump may be connected to the aorta with a T insert 55 and end-to-end grafts 56 as shown in FIG. 15. In the FIG. 17 embodiment, the outlet conduit 51' is connected to the aorta with a T-insert 55, with a flap-type check valve 61 placed in the T connector 55. Other alternative embodiments are available: for example, a bifurcated flow path, of the type illustrated in FIGS. 3, could be used with a flap-type check valve normally blocking the path through a secondary shunt conduit. Similarly, in an encapsulated pump, as illustrated in FIG. 1C, with an encapsulated emergency shunt flow path 207, a flap type check valve could also be used in place of an occluder.

Figure 18:
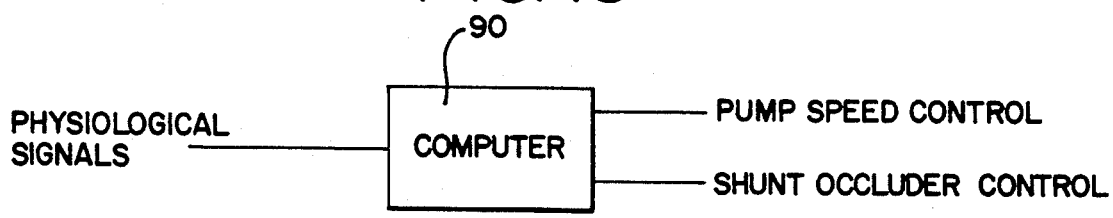
FIG. 18 is a diagram illustrating control of the pump and control of the shunt occluder, should such control be necessary.

The flow enhancer may be controlled to complement the pumping action of the heart. In particular, use of a centrifugal pump makes a wide range of flow rates available since the pump input varies with rotational speed and the pump output varies with input and with exit resistance. A simple controller, to control the rotational speed of the centrifugal pump, may be set to cause the centrifugal pump to operate at a number of different preselected levels; with transcutaneous access to the device, the patient may control the pump speed depending upon anticipated activities. A more complex controller could also be employed, as illustrated in FIG. 18. Selected physiological conditions of the subject are sensed and connected with an implanted computer 90. Employing sensing systems such as those used in present state of the art cardiac pacemakers. The computer provides pump speed control signals and, if needed, shunt occluder control signals, as indicated in FIG. 18. For example, to increase or decrease preload of the heart in response to either a directly measured left atrial pressure or to an indirect lateral wall distending pressure; 2) to respond to physiological demand as indicated by signals produced by muscular activity, increased cerebral potential for emotional phenomena, or the level of blood oxygen saturation in the mixed venous circuit (obtained in a branch of the pulmonary artery) which falls with increased peripheral oxygen extraction secondary to low cardiac output or increased peripheral oxygen or tissue demand.

Furthermore, pump speed may be modulated to provide a limited pulsing of the blood during systole and diastole. More particularly, the pulsing of the blood flow may be timed to key segments of systole and diastole.

Figure 19:
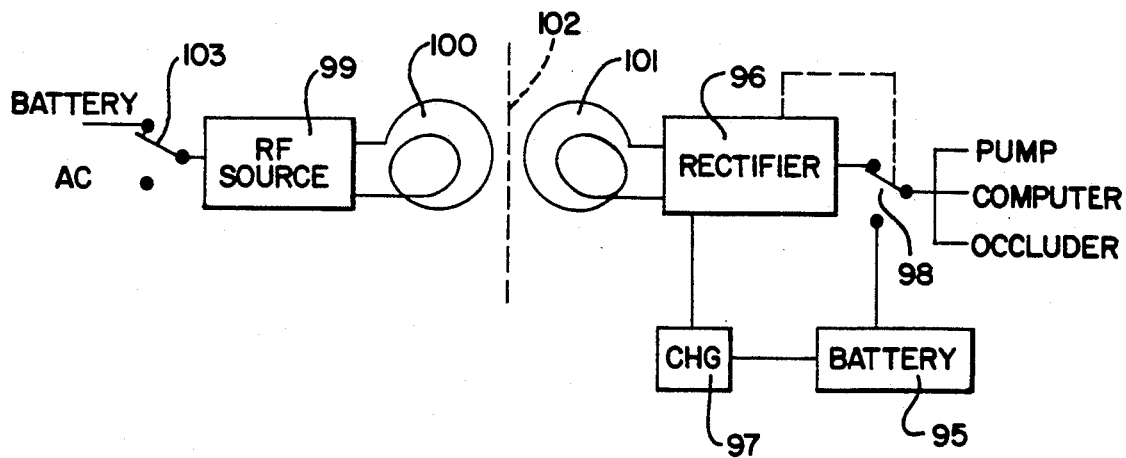
FIG. 19 is a diagram of the electrical system for powering the flow enhancer pump and occluder, should power for the occluder be needed.

The cardiovascular flow enhancer is preferably embodied in a system as shown in FIG. 19. Implanted with the pump, computer and occluder are a battery 95, a rectifier 96, battery charge control 97 and a switch 98. The system uses a readily available transcutaneous power transfer package. An external RF source 99 is connected with a transmitter coil 100. A receiver coil 101 is imlanted immediately under the subject's skin 102 and is connected with rectifier 96. To charge the battery, the subject places the transmitter coil 100 outside the skin 102 adjacent receiver coil 101. The RF source may be powered from either a battery or an AC supply selected through switch 103. RF power is coupled from the transmitter coil 100 to the receiver coil 101. Rectifier 96 rectifies the RF power and provides DC power through switch 98 to the pump, computer and occluder and to battery charger 97. When the battery 95 is charged, the external RF source may be removed. The pump, computer and occluder are powered from battery 95 through switch 98.

I claim:

1. A method of implanting a cardiovascular flow enhancer comprising the steps of:
providing an implantable centrifugal pump having an inlet and an outlet;
providing an inlet conduit;
providing an outlet conduit;
connecting the inlet conduit with the pump inlet and with the descending thoracic aorta at substantially the site of the pressure node for blood from the heart to receive blood from the descending thoracic aorta and direct blood to the pump; and
connecting the outlet conduit with the pump outlet and with the descending thoracic aorta at a point downstream from the inlet connection to discharge blood into the aorta.

2. The method of implanting a cardiovascular flow enhancer as claimed in claim 1 wherein the outlet conduit is connected with the descending thoracic aorta at substantially the last blood flow and pressure antinode before the heart of the descending thoracic aorta.

3. The method of implanting a cardiovascular flow enhancer as claimed in claim 1 in which the pump is located above the diaphragm in the lower left hemithorax of the posterior chest.

4. The method of implanting a cardiovascular flow enhancer as claimed in claim 1 in which the pump is located in the upper left hemithorax of the posterior chest.

5. A method of implanting a cardiovascular flow enhancer comprising the steps of:
providing an implantable centrifugal pump having an inlet and an outlet;
providing an inlet conduit;
providing an inlet conduit;
providing an outlet conduit;
connecting the inlet conduit with the pump inlet and with the descending thoracic aorta at substantially the site of the pressure node for blood from the heart to receive blood from the aorta and direct blood to the pump; and
connecting the outlet conduit with the pump outlet and with the descending thoracic aorta at a point downstream from the inlet connection to discharge blood into the aorta;
providing an alternative flow path in shunt with the pump to provide an emergency blood flow path around the pump.

6. The method of implanting a cardiovascular flow enhancer as claimed in claim 5 wherein a section of the thoracic aorta is connected in shunt with the pump.

7. The method of implanting a cardiovascular flow enhancer as claimed in claim 5 further comprising providing a controllable occluder operatively associated with the alternate flow path, the occluder being operable to minimize blood flow through the flow path in shunt with the pump during normal operation of the pump and to allow greater blood flow through the shunt conduit when blood flow through the pump falls below a minimum level.

8. The method of implanting a cardiovascular flow enhancer as claimed in claim 5 wherein the alternate flow path comprises an expandable graft conduit having an inner diameter permitting minimal blood flow through the shunt conduit when the pump is in normal operation, the expandable graft conduit being expandable to allow greater blood flow through the conduit when blood flow through the pump falls below a minimum level.

9. The method of implanting a cardiovascular flow enhancer as claimed in claim 5 wherein the alternate flow path includes a check valve to prevent back flow through the alternate flow path, and wherein the check valve is openable to allow blood flow through the alternate flow path when pressure upstream of the check valve reaches a predetermined maximum level.

10. A method of implanting a cardiovascular flow enhancer comprising the steps of:
providing a centrifugal pump having an inlet and an outlet;
connecting the pump inlet to receive blood from the descending thoracic aorta from a site at substantially the first quiescent section of the descending thoracic aorta downstream from the brachiocephalic arteries; and
connecting the pump outlet to discharge blood to the descending thoracic aorta at a point downstream from the inlet connection.

11. A method of implanting a cardiovascular flow enhancer comprising the steps of:
providing a centrifugal pump having an inlet and an outlet;
connecting the pump inlet to receive blood from the proximal descending thoracic aorta; and
connecting the pump outlet to discharge blood to the descending thoracic aorta at a point downstream from the inlet connection.

12. The method of implanting a cardiovascular flow enhancer as claimed in claim 11 wherein the pump inlet is connected to receive blood from a site about one to twelve centimeters downstream from the juncture of the left subclavian artery and the aorta.

13. A method of improving cardiovascular performance comprising the steps of:
providing a centrifugal pump having an inlet and an outlet;
connecting the pump inlet to receive blood from the first pressure and flow node of the descending thoracic aorta; and
connecting the pump outlet to discharge blood to the descending thoracic aorta at a point downstream of the first connection.

14. The method of improving cardiovascular performance of claim 13 further comprising:
providing an inlet conduit having one end in fluid communication with the pump inlet;
providing an outlet conduit having one end in fluid communication with the pump outlet;
connecting the other end of the inlet conduit to the descending thoracic aorta substantially at the first nodal point; and connecting the other end of the outlet conduit to the descending thoracic aorta at a point downstream of the connection of the inlet conduit to the descending thoracic aorta.

15. The method of improving cardiovascular performance of claim 14 further comprising providing an inlet chamber in fluid connection with the pump inlet and the inlet conduit, an outlet chamber in fluid communication with the outlet conduit and the pump outlet, and a housing holding the pump, inlet chamber and outlet chamber.

16. The method of improving cardiovascular performance of claim 15 further comprising providing an emergency shunt flow path between the inlet chamber and the outlet chamber, the emergency shunt flow path being held within said housing.

17. The method of improving cardiovascular performance of claim 15 further comprising providing a drive motor within the housing to drive the pump.

18. The method of improving cardiovascular performance of claim 13 further comprising the steps of:
sensing physiological conditions of the subject; and
varying pump speed in accordance with the sensed physiological conditions of the subject.

19. A cardiovascular flow enhancer comprising:
a centrifugal pump having an inlet and an outlet;
an inlet conduit having one end in fluid communication with the pump inlet;
an outlet conduit having one end in fluid communication with the pump outlet;
the centrifugal pump, inlet conduit and outlet conduit defining a primary blood flow path; and
a parallel flow conduit extending between the inlet and outlet conduits to provide an emergency blood flow path for a level of blood flow when blood flow through the pump falls below a minimum level and to provide a secondary blood flow path for a lower level of blood flow during normal operation of the pump, the parallel flow conduit being in parallel with the primary blood flow path the cardiovascular flow enhancer further comprising a housing made of a biologically inert material within which the centrifugal pump and parallel flow conduit are held, said housing being configured and sized to be implanted in a living body.

20. The cardiovascular flow enhancer of claim 19 further comprising a controllable occluder operatively associated with the parallel flow conduit to limit blood flow through the parallel flow conduit during normal operation of the pump and to allow greater blood flow through the parallel flow conduit when blood flow through the pump falls below a minimum level.

21. The cardiovascular flow enhancer of claim 19 wherein the parallel flow conduit is expandable and has an inner diameter permitting minimal blood flow through the shunt conduit when the pump is in normal operation, the parallel flow conduit being expandable to allow greater blood flow through the conduit when blood flow through the pump falls below a minimum level.

22. The cardiovascular flow enhancer of claim 19 further comprising a flap valve to limit blood flow through the parallel flow conduit, the flap valve being openable to allow blood flow through the parallel flow conduit when pressure upstream of the flap valve reaches a predetermined maximum level.

23. The cardiovascular flow enhancer of claim 19 wherein the inlet conduit defines an inlet chamber in fluid communication with the pump inlet and the outlet conduit defines an outlet chamber in fluid communication with the pump outlet, the inlet and outlet chambers being held within the housing and the parallel flow conduit extending between the inlet chamber and the outlet chamber.

* * * * *